(12) United States Patent
Marvel

(10) Patent No.: US 6,531,141 B1
(45) Date of Patent: Mar. 11, 2003

(54) OIL-IN-WATER EMULSION CONTAINING TRETINOIN

(75) Inventor: John Marvel, East Brunswick, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/521,445

(22) Filed: Mar. 7, 2000

(51) Int. Cl.$^7$ .............................. A61K 6/00; A61K 7/00
(52) U.S. Cl. ...................... 424/401; 424/400; 424/450; 424/59; 424/78.02; 424/78.03; 424/78.05; 514/844; 514/937; 514/938
(58) Field of Search ................................ 424/400, 401, 424/59, 78.02; 514/844, 937, 938

(56) References Cited

U.S. PATENT DOCUMENTS

| | | | |
|---|---|---|---|
| 2,897,119 A | | 7/1959 | Dunn et al. |
| 3,906,108 A | | 9/1975 | Felty |
| 4,190,594 A | * | 2/1980 | Gander et al. .............. 260/404 |
| 4,214,000 A | | 7/1980 | Papa |
| 4,247,547 A | | 1/1981 | Marks |
| 4,466,805 A | | 8/1984 | Welters et al. |
| 4,551,480 A | | 11/1985 | Stiefel et al. |
| 4,603,146 A | | 7/1986 | Kligman |
| 4,720,353 A | | 1/1988 | Bell |
| 4,826,828 A | | 5/1989 | Wilmott et al. |
| 4,877,805 A | | 10/1989 | Kligman |
| 5,023,235 A | | 6/1991 | N'Guyen et al. |
| 5,034,228 A | | 7/1991 | Meybeck et al. |
| 5,484,816 A | | 1/1996 | Yanagida et al. |
| 5,559,149 A | | 9/1996 | Clum et al. |
| 5,646,186 A | * | 7/1997 | Wang et al. ................. 514/557 |
| 5,652,263 A | | 7/1997 | Clum et al. |
| 5,976,555 A | * | 11/1999 | Liu et al. ..................... 424/401 |
| 6,024,941 A | | 2/2000 | Yanigada et al. |
| 6,080,393 A | | 6/2000 | Liu et al. |
| 6,193,956 B1 | | 2/2001 | Liu et al. |

FOREIGN PATENT DOCUMENTS

| | | |
|---|---|---|
| DE | 3514724 C2 | 4/1985 |
| EP | 0 094 771 B1 | 5/1983 |
| EP | 0 330 496 B1 | 2/1989 |
| EP | 0 343 444 B1 | 5/1989 |
| EP | 0 391 033 A2 | 2/1990 |
| EP | 0 408 370 B1 | 7/1990 |
| EP | 0 421 333 A1 | 10/1990 |
| EP | 0 440 398 A1 | 1/1991 |
| FR | 3400 M | 5/1964 |
| JP | 53 14607 | 5/1978 |
| JP | 58 41813 | 3/1983 |
| WO | WO95/26709 A1 | 10/1995 |

OTHER PUBLICATIONS

Copy of packaging of product Retin–A–Gel (tretinoin) 0.01% and enclosed pamphlet.
Copy of packaging of product Retin–A–Gel (tretinoin) 0.025% and enclosed pamphlet.
Copy of packaging of product Retin–A–Liquid (tretinoin) 0.05% and enclosed pamphlet.
Copy of packaging of product Retin–A Cream (tretinoin) 0.1% and enclosed pamphlet.
Copy of packaging of Retin–A Cream (tretinoin) 0.025% and enclosed pamphlet.
Copy of packaging of Retin–A Cream (tretinoin) 0.05% and enclosed pamphlet.
Copy of packaging of Retin–A Micro (tretinoin gel) microsphere, 0.1% and enclosed pamphlet.
Copy of packaging of Renova (tretinoin emollient cream) 0.05% and enclosed pamphlet.
Copy of Renova (tretinoin emollient cream) 0.05% guide to success pamphlet.
Prescription Pharmacy, $2^{nd}$ Ed., (1970) J.B. Sprowls, Jr., p. 220–223.
Product Data Sheet for Vitamin A Alcohol Blend, Roche, 1988.
Buhker, V., Vademecum for Vitamin Formulations, 1988.
Dittert, L.W. Sprowls' American Pharmacy, $7^{th}$ Ed., p. 471 (1974).
McCutcheon's Emulsifier's and Detergents, vol. 1 p. 250 (1991).
Remington's Pharmaceutical Sciences, $15^{th}$ Ed. (1975) p. 329–337.

* cited by examiner

Primary Examiner—Thurman K. Page
Assistant Examiner—Charesse Evans
(74) Attorney, Agent, or Firm—William E. McGowan

(57) ABSTRACT

The present invention relates to an oil-in-water emulsion containing tretinoin and the use thereof in mitigating skin disorders such as acne, photodamaged skin, wrinkles, mottled hyperpigmentation, tactile roughness, and yellowing of facial skin.

26 Claims, No Drawings

OIL-IN-WATER EMULSION CONTAINING TRETINOIN

FIELD OF THE INVENTION

The present invention relates to an oil-in-water emulsion containing tretinoin and the use thereof in mitigating skin disorders such as acne, photodamaged skin, wrinkles, mottled hyperpigmentation, tactile roughness, and yellowing of facial skin.

BACKGROUND OF THE INVENTION

Tretinoin, or all-trans-retinoic acid, is a naturally occurring retinoid and is the major metabolite of Vitamin A. Tretinoin modulates the expression and function of numerous genes by binding to intracellular receptors, termed retinoic acid receptors, both in the cytosol and nucleus. The action of tretinoin at the receptor level accounts for its wide-ranging effects on skin function, and tretinoin acts on many skin cell types. The ability of tretinoin to pharmacologically regulate multiple skin cells likely explains why it decreases fine and coarse wrinkles, reduces melanocytic hyperpigmentation, and improves skin texture (tactile smoothening).

Although the exact mechanism of action is unknown, tretinoin is also the only topical anti-acne agent available by prescription that is believed to be effective against the microcomedo, the precursor to the lesion in acne. Topical tretinoin products ranging in concentration from 0.01% to 0.1% in different vehicles, including an oil-in-water emulsion cream, have been marketed in the United States for the treatment of acne vulgaris under the brand name Retin-A® since 1971.

While the above formulations have been effective in mitigating the above mentioned skin disorders, skin irritation of varying severity may be observed. The present invention, thus, relates to a novel oil-in-water emulsion composition containing tretinoin that has reduced skin irritation properties.

SUMMARY OF THE INVENTION

In one aspect, the invention features an oil-in-water emulsion comprising: (i) about 0.001% to about 1%, by weight, of tretinoin; (ii) about 5% to about 20%, by weight, of caprylic/capric triglyceride; (iii) about 1% to about 10%, by weight, of a $C_{30}$–$C_{100}$ polyalkylene glycol ether of a $C_{10}$–$C_{30}$ fatty alcohol such as the $C_{40}$ polyethylene ether of a $C_{10}$–$C_{30}$ fatty alcohol such as steareth-20, isoceteth-20, beheneth-20, oleth-20, ceteth-20, laureth-20, and ceteareth-20; (iv) about 0.1% to about 5%, by weight, of a $C_4$–$C_{30}$ polyalkylene glycol ether of a $C_{10}$–$C_{30}$ fatty alcohol such as the $C_4$ polyethylene ether of a $C_{10}$–$C_{30}$ fatty alcohol such as steareth-2, ceteth-2, laureth-2, and oleth-2, the $C_8$ polyethylene ethers of a $C_{10}$–$C_{30}$ fatty alcohol such as laureth-4, and the $C_{24}$ polyethylene ethers of a $C_{10}$–$C_{30}$ fatty alcohol such as ceteareth-24; (v) about 0% to about 10%, by weight, of a $C_{10}$–$C_{30}$ fatty acid such as stearic acid, capric acid, lauric acid, myristic acid, pentadecanoic acid, palmitic acid, isostearic acid, behenic acid, margaric acid, novadecanoic acid, cerotic acid, montanic acid, and melissic acid) (e.g., the emulsion may not comprise of a $C_{10}$–$C_{30}$ fatty acid); (vi) about 1% to about 10%, by weight, of a first $C_{10}$–$C_{30}$ fatty alcohol (e.g., cetyl alcohol, decyl alcohol, isodecyl alcohol, lauryl alcohol, isostrearyl alcohol, stearyl alcohol, behenyl alcohol, cetearyl alcohol, myristyl alcohol, and isocetyl alcohol); (vii) about 0% to about 10%, by weight, of a second $C_{10}$–$C_{30}$ fatty alcohol; and (viii) about 50% to about 90%, by weight, of water.

The C value before the polyalkylene glycol ether is the average number of carbons in the polyethylene glycol group. In one embodiment, the $C_{30}$–$C_{100}$ polyalkylene glycol ether of a $C_{10}$–$C_{30}$ fatty alcohol is a hydrophilic compound and the $C_4$–$C_{30}$ polyalkylene glycol ether of a $C_{10}$–$C_{30}$ fatty alcohol is a lipophilic compound.

In one embodiment, the oil-in-water emulsion further comprises: (ix) about 0.1% to about 1%, by weight, of xanthan gum; (x) about 0.001% to about 1%, by weight, of a preservative (e.g., benzyl alcohol or a paraben such as propylparaben, methylparaben, ethylparaben, and butylparaben, sorbic acid, and chlorocresol); (xi) about 0.001% to about 1%, by weight, of an antioxidant (e.g., butylated hydroxytoluene, tocopherols, and ascorbic acid); (xii) about 0.001% to about 1%, by weight, of a chelating agent (e.g., edetate disodium); and (xiii) about 0% to about 1%, by weight, of a fragrance (e.g, Chemoderm 6401B).

In one aspect, the invention features a method of mitigating a skin condition in a human selected from the group consisting of acne, photodamaged skin, wrinkles (e.g., fine wrinkles), mottled hyperpigmentation, tactile roughness, and yellowing of facial skin, the method comprising topically administering to the skin of the human the above oil-in-water emulsion.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative and are not limited by the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to an oil-in-water emulsion containing tretinoin and the use thereof in mitigating skin disorders such as acne, photodamaged skin, wrinkles, mottled hyperpigmentation, tactile roughness, and yellowing of facial skin. The amount of tretinoin in the emulsion varies depending on the skin condition being treated, the manner of administration, and the age and body weight of the subject.

The compositions of the present invention can be administered topically to a human, e.g., by the direct laying on or spreading of the emulsion on the skin of a human (e.g., daily before retiring). Examples of suitable antioxidants (e.g., ascorbic acid, tocopherols, butylated hydroxyanisole ("BHA"), and butylated hydroxytoluene ("BHT")), preservatives (e.g., parabens such as methylparaben and propylparaben), and chelating agents (e.g., such as EDTA and edetate disodium) are listed in the International Cosmetic Ingredient Dictionary and Handbook, eds. Wenninger and McEwen, pp. 1612–13, 1626, and 1654–55 (The Cosmetic, Toiletry, and Fragrance Assoc., Washington, D.C., $7^{th}$ Edition, 1997) (hereinafter "ICI Handbook").

In one embodiment, the emulsion further comprises another dermatologically active agent. What is meant by a "dermatologically active agent" is a compound that has a cosmetic or therapeutic effect on the skin. In one embodiment, the agent is selected from the group consisting of hydroxy acids, benzoyl peroxide, sulfur resorcinol, ascorbic acid, D-panthenol, hydroquinone, sunscreen agents, antiinflammatory agents, skin lightening agents, antimicrobial and antifungal agents, estrogens, and derivatives and mixtures thereof. The dermatologically active agent will typically be present in the composition of the invention in an amount of from about 0.001% to about 20% by weight of the composition, e.g., about 0.01% to about 10%, e.g., about 0.1% to about 5%.

Examples of hydroxy acids include, but are not limited to, (i) alpha-hydroxy acids such as glycolic acid, lactic acid, malic acid, citric acid, and tartaric acid, (ii) beta-hydroxy acids such as salicylic acid, and/or (iii) polyhydroxy acids. See, e.g., European Patent Application No. 273,202.

Examples of derivatives of ascorbic acid include, but are not limited to, ascorbyl palmitate, magnesium ascorbyl phosphate, sodium ascorbyl phosphate, zinc ascorbyl phosphate, ascorbyl glucoside, sodium ascorbate, and ascorbyl polypeptide. An example of a derivative of hydroquinone includes, but is not limited to, arbutin.

The emulsions of the subject invention may contain, in addition to the aforementioned components, a wide variety of additional oil-soluble materials and/or water-soluble materials conventionally used in topical compositions, at their art-established levels. Examples of such materials are disclosed in the ICI Handbook, pp.1607–1697.

The emulsions of the present invention may be prepared using methodology that is well known by an artisan of ordinary skill. The following is a description of the manufacturing and testing of specific emulsions of the present invention.

EXAMPLE I

Synthesis of Oil-in-Water Emulsion Containing 0.02% Tretinoin

An oil-in-water emulsion containing 0.02% tretinoin (0.022% of tretinoin was added as a 10% overage during synthesis to account of loss during manufacture and/or loss due to stability during storage) was synthesized as follows. The ingredients, and weight percentage of such ingredients, are listed below in Table I.

TABLE I

| INGREDIENTS | % BY WEIGHT |
| --- | --- |
| Oil Phase | |
| Caprylic/Capric Triglyceride | 10.00 |
| Steareth 20 | 4.15 |
| Stearic Acid | 4.00 |
| Cetyl Alcohol | 4.00 |
| Stearyl Alcohol | 3.00 |
| Steareth 2 | 0.85 |
| Methylparaben | 0.20 |
| Propylparaben | 0.10 |
| Butylated Hydroxytoluene | 0.10 |
| Tretinoin | 0.022 |
| Aqueous Phase | |
| Benzyl Alcohol | 1.00 |
| Xanthan Gum | 0.30 |

TABLE I-continued

| INGREDIENTS | % BY WEIGHT |
| --- | --- |
| Edetate Disodium | 0.05 |
| Purified Water | q.s. 1.00 |
| Post-Emulsification Phase | |
| Chemoderm 6401/B | 0.10 |

The water phase ingredients were mixed together at approximately 65° C. (i.e., 60° C. to 70° C.). The oil phase ingredients were also separately mixed together at approximately 65° C. The two phases were then combined, mixed using a high shear mixer, and allowed to cool to approximately 48° C. (i.e., 43° C. to 53° C.). Next the Chemoderm 6401/B was then added, and the mixture was then cooled to approximately 34° C. (i.e., 20° C. to 35° C.). The resulting oil-in-water emulsion can then be packaged (e.g., into a lined, blind-ended aluminum tube with a polyethylene spike cap). Other concentrations of the product (e.g., 0.05% tretinoin).

EXAMPLE II

Synthesis of Oil-in-Water Emulsion Containing 0.05% Tretinoin

An oil-in-water emulsion containing 0.05% tretinoin (0.055% of tretinoin was added during synthesis to account of loss during manufacture and/or loss due to stability during storage) was synthesized as set forth in Example I except that 0.055%, by weight, of tretinoin was added in place of 0.022% tretinoin.

EXAMPLE III

Synthesis of Oil-in-Water Emulsion Containing 0.02% Tretinoin

An oil-in-water emulsion containing 0.02% tretinoin (0.021% of tretinoin was added during synthesis to account of loss during manufacture and/or loss due to stability during storage) was synthesized as set forth in Example I except that: (i) 0.021%, by weight, of tretinoin was added in place of 0.022% tretinoin; (ii) stearic acid and Chemoderm 6401B were not added; (iii) 5.5%, by weight, of cetyl alcohol was added in place of 4%, by weight, of cetyl alcohol; and (iv) 5.5%, by weight, of stearyl alcohol was added in place of 3%, by weight, of stearyl alcohol.

EXAMPLE IV

Synthesis of Oil-in-Water Emulsion Containing 0.05% Tretinoin

An oil-in-water emulsion containing 0.05% tretinoin (between about 0.05% to about 0.055% of tretinoin may be added during synthesis to account of loss during manufacture and/or loss due to stability during storage) was synthesized as set forth in Example IIII except that between about 0.05% and 0.055%, by weight, of tretinoin was added in place of 0.021% tretinoin.

EXAMPLE V

Human Phase I Cumulative Irritation Study

The objective of the study was to evaluate the cumulative irritation potential of two oil-in-water emulsions of Examples I and II with the commercial products Retin-A® Cream 0.05% and Retin-A® Cream 0.025% (sold by Ortho Dermatological, Skillman, NJ). The Retin-A® Creams are oil-in-water emulsions having a different formulation as they contain isopropyl myristate rather than caprylic/capric triglyceride as the solubilizer of the tretinoin and they only one emulsifier (polyoxyl 40 stearate) rather than the two emulsifiers of the present invention (e.g., Steareth-20 and Steareth-2).

The study was a single-center, double-blind, controlled, randomized Phase I study using 25 healthy Caucasian volunteers ages 19 to 60 (mean of 44). Of the twenty-five subjects, 20 were female. The study drugs were each applied daily on semi-occlusive patches to each subject's back five times weekly for three weeks. Each site was evaluated 24 hours (or 72 hours on weekends) after each application and scored in a range of 0–4 for the severity of irritation (a score of 0 indicating no irritation). Twenty-three subjects completed the study as two subjects were lost to follow-up after one study drug application.

Table II lists the total cumulative irritation scores after two-weeks (maximum score 920) and three-weeks (maximum score 1380) for those completing the study.

TABLE II

| STUDY DRUG | 2-WEEK | 3-WEEK |
| --- | --- | --- |
| Retin-A ® Cream (0.05% tretinoin) | 78.5 | 267.5 |
| Example II (0.05% tretinoin) | 54.5 | 200.0 |
| Retin-A ® Cream (0.025% tretinoin) | 59.5 | 181.0 |
| Example I (0.02% tretinoin) | 24.5 | 92.5 |

The oil-in-water emulsions of Example I and II, thus, unexpectedly reduced the irritation associated with the drug tretinoin. For example, Retin-A® Cream (0.05%) exhibited an increase in irritation of 44% at week 2 and 33% at week 3 as compared to the emulsion of Example II having the same amount of tretinoin. Even more surprising, Retin-A® Cream (0.025% tretinoin) exhibited an increase of 142% at week 2 and 96% at week 3 as compared to the emulsion of Example I having almost the same amount of tretinoin.

EXAMPLE VI

Human Phase I Cumulative Irritation Study

A similar study was conducted to evaluate the cumulative irritation potential of the two oil-in-water emulsions of Examples II and IV.

The study was a single-center, double-blind, controlled, randomized Phase I study using 25 healthy Caucasian volunteers ages 18 to 60. The study drugs were each applied daily on semi-occlusive patches to each subject's back five times weekly for three weeks. Each site was evaluated 24 hours (or 72 hours on weekends) after each application and scored in a range of 0–4 for the severity of irritation (a score of 0 indicating no irritation).

Table III lists the total cumulative irritation scores after two-weeks (maximum score 1000) and three-weeks (maximum score 1500).

TABLE III

| STUDY DRUG | 2-WEEK | 3-WEEK |
| --- | --- | --- |
| Example II (0.05% tretinoin) | 58.5 | 284.5 |
| Example IV (0.05% tretinoin) | 55.5 | 257.5 |

The oil-in-water emulsions of Examples II and IV, thus, had similar low findings of irritation.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. An oil-in-water emulsion comprising:
   (i) about 0.001% to about 1%, by weight, of tretinoin;
   (ii) about 5% to about 20%, by weight, of caprylic/capric triglyceride;
   (iii) about 1% to about 10%, by weight, of a $C_{30}$–$C_{100}$ polyethylene glycol ether of a $C_{10}$–$C_{30}$ fatty alcohol;
   (iv) about 0.1% to about 5%, by weight, of a $C_4$–$C_{30}$ polyethylene glycol ether of a $C_{10}$–$C_{30}$ fatty alcohol;
   (v) about 0% to about 10%, by weight, of a $C_{10}$–$C_{30}$ fatty acid;
   (vi) about 1% to about 10%, by weight, of a first $C_{10}$–$C_{30}$ fatty alcohol;
   (vii) about 0% to about 10%, by weight, of a second $C_{10}$–$C_{30}$ fatty alcohol; and
   (viii) about 50% to about 90%, by weight, of water.

2. An oil-in-water emulsion of claim 1 further comprising:
   (ix) about 0.1% to about 1%, by weight, of xanthan gum;
   (x) about 0.001% to about 1%, by weight, of a preservative;
   (xi) about 0.001% to about 1%, by weight, of an antioxidant;
   (xii) about 0.001% to about 1%, by weight, of a chelating agent; and
   (xiii) about 0% to about 1%, by weight, of a fragrance.

3. An oil-in-water emulsion of claim 2, said emulsion comprising:
   (i) about 0.001% to about 1%, by weight, of tretinoin;
   (ii) about 5% to about 20%, by weight, of caprylic/capric triglyceride;
   (iii) about 1% to about 10%, by weight, of steareth-20;
   (iv) about 0.1% to about 5%, by weight, of steareth-2;
   (v) about 0% to about 10%, by weight, of stearic acid;
   (vi) about 1% to about 10%, by weight, of cetyl alcohol;
   (vii) about 1% to about 10%, by weight, of stearyl alcohol;
   (viii) about 50% to about 90%, by weight, of water;
   (ix) about 0.1% to about 1%, by weight, of xanthan gum;
   (x) about 0.001% to about 1%, by weight, of a mixture of propylparaben and methylparaben and about 0.1% to about 5%, by weight, of benzyl alcohol;
   (xi) about 0.001% to about 1%, by weight, of butylene hydroxytoluene;
   (xii) about 0.001% to about 1%, by weight, of edetate disodium; and
   (xiii) about 0% to about 1%, by weight, of Chemoderm 6401B.

4. An oil-in-water emulsion of claim 1, wherein said emulsion comprises:
   (i) about 0.01% to about 1%, by weight, of tretinoin;
   (ii) about 10%, by weight, of caprylic/capric triglyceride;
   (iii) about 4%, by weight, of steareth-20;
   (iv) about 0.8%, by weight, of steareth-2;
   (v) about 0% to about 4%, by weight, of stearic acid;
   (vi) about 4% to about 6%, by weight, of cetyl alcohol;
   (vii) about 3% to about 6%, by weight, of stearyl alcohol; and
   (viii) about 72%, by weight, of water.

5. An oil-in-water emulsion of claim 4 further comprising:
   (ix) about 0.3% of xanthan gum;
   (x) about 0.1%, by weight, of propylparaben, about 0.2%, by weight, of methylparaben; and about 1%, by weight, of benzyl alcohol;
   (xi) about 0.1%, by weight, of butylated hydroxytoluene;
   (xii) about 0.05%, by weight, of edetate disodium; and
   (xiii) about 0% to about 0.01%, by weight, of Chemoderm 6401B.

6. An oil-in-water emulsion of consisting essentially of:
   (i) about 0.01% to about 1%, by weight, of tretinoin;
   (ii) about 10%, by weight, of caprylic/capric triglyceride;
   (iii) about 4%, by weight, of steareth-20;
   (iv) about 0.8%, by weight, of steareth-2;
   (v) about 0% to about 4%, by weight, of stearic acid;
   (vi) about 4% to about 6%, by weight, of cetyl alcohol;
   (vii) about 3% to about 6%, by weight, of stearyl alcohol;
   (viii) about 72%, by weight, of water;
   (ix) about 0.3% of xanthan gum;
   (x) about 0.1%, by weight, of propylparaben, about 0.2%, by weight, of methylparaben, and about 1%, by weight, of benzyl alcohol;
   (xi) about 0.1%, by weight, of butylated hydroxytoluene;
   (xii) about 0.05%, by weight, of edetate disodium; and
   (xiii) about 0% to about 0.01%, by weight, of Chemoderm 6401B.

7. An oil-in-water emulsion of consisting of:
   (i) about 0.01% to about 1%, by weight, of tretinoin;
   (ii) about 10%, by weight, of caprylic/capric triglyceride;
   (iii) about 4%, by weight, of steareth-20;
   (iv) about 0.8%, by weight, of steareth-2;
   (v) about 4%, by weight, of stearic acid;
   (vi) about 4%, by weight, of cetyl alcohol;
   (vii) about 3%, by weight, of stearyl alcohol;
   (viii) about 72%, by weight, of water;
   (ix) about 0.3% of xanthan gum;
   (x) about 0.1%, by weight, of propylparaben, about 0.2%, by weight, of methylparaben, and about 1%, by weight, of benzyl alcohol;
   (xi) about 0.1%, by weight, of butylated hydroxytoluene;
   (xii) about 0.05%, by weight, of edetate disodium; and
   (xiii) about 0.01%, by weight, of Chemoderm 6401B.

8. An oil-in-water emulsion of consisting of:
   (i) about 0.01% to about 1%, by weight, of tretinoin;
   (ii) about 10%, by weight, of caprylic/capric triglyceride;
   (iii) about 4%, by weight, of steareth-20;
   (iv) about 0.8%, by weight, of steareth-2;
   (v) about 5%, by weight, of cetyl alcohol;
   (vi) about 5%, by weight, of stearyl alcohol;
   (vii) about 72%, by weight, of water;
   (viii) about 0.3% of xanthan gum;
   (ix) about 0.1%, by weight, of propylparaben, about 0.2%, by weight, of methylparaben, and about 1%, by weight, of benzyl alcohol;
   (x) about 0.1%, by weight, of butylated hydroxytoluene; and
   (xi) about 0.05%, by weight, of edetate disodium.

9. An oil-in-water emulsion of claim 1, wherein said emulsion comprises about 0.02%, by weight, of tretinoin.

10. An oil-in-water emulsion of claim 7, wherein said emulsion comprises about 0.02%, by weight, of tretinoin.

11. An oil-in-water emulsion of claim 8, wherein said emulsion consists of about 0.02%, by weight, of tretinoin.

12. An oil-in-water emulsion of claim 1, wherein said emulsion comprises about 0.05%, by weight, of tretinoin.

13. An oil-in-water emulsion of claim 7, wherein said emulsion comprises about 0.05%, by weight, of tretinoin.

14. An oil-in-water emulsion of claim 8, wherein said emulsion consists of about 0.05%, by weight, of tretinoin.

15. A method of mitigating a skin condition in a human selected from the group consisting of acne, photodamaged skin, wrinkles, mottled hyperpigmentation, tactile roughness, and yellowing of facial skin, said method comprising topically administering to the skin of said human an oil-in-water emulsion comprising:
   (i) about 0.001% to about 1%, by weight, of tretinoin;
   (ii) about 5% to about 20%, by weight, of caprylic/capric triglyceride;
   (iii) about 1% to about 10%, by weight, of a $C_{30}$–$C_{100}$ polyethylene glycol ether of a $C_{10}$–$C_{30}$ fatty alcohol;
   (iv) about 1% to about 10%, by weight, of a $C_4$–$C_{30}$ polyethylene glycol ether of a $C_{10}$–$C_{30}$ fatty alcohol;
   (v) about 0% to about 10%, by weight, of a $C_{10}$–$C_{30}$ fatty acid;
   (vi) about 1% to about 10%, by weight, of a first $C_{10}$–$C_{30}$ fatty alcohol;
   (vii) about 0% to about 10%, by weight, of a second $C_{10}$–$C_{30}$ fatty alcohol; and
   (viii) about 50% to about 90%, by weight, of water.

16. A method of mitigating a skin condition in a human selected from the group consisting of acne, photodamaged skin, wrinkles, mottled hyperpigmentation, tactile roughness, and yellowing of facial skin, said method comprising topically administering to the skin of said human an oil-in-water emulsion consisting of:
   (i) about 0.01% to about 1%, by weight, of tretinoin;
   (ii) about 10%, by weight, of caprylic/capric triglyceride;
   (iii) about 4%, by weight, of steareth-20;
   (iv) about 0.8%, by weight, of steareth-2;
   (v) about 4%, by weight, of stearic acid;
   (vi) about 4%, by weight, of cetyl alcohol;
   (vii) about 3%, by weight, of stearyl alcohol;
   (viii) about 72%, by weight, of water;
   (ix) about 0.3% of xanthan gum;
   (x) about 0.1%, by weight, of propylparaben, about 0.2%, by weight, of methylparaben, and about 1%, by weight, of benzyl alcohol;

(xi) about 0.1%, by weight, of butylated hydroxytoluene;

(xii) about 0.05%, by weight, of edetate disodium; and (xiii) about 0.01%, by weight, of Chemoderm 6401B.

17. A method of mitigating a skin condition in a human selected from the group consisting of acne, photodamaged skin, wrinkles, mottled hyperpigmentation, tactile roughness, and yellowing of facial skin, said method comprising topically administering to the skin of said human an oil-in-water emulsion consisting of:

(i) about 0.01% to about 1%, by weight, of tretinoin;

(ii) about 10%, by weight, of caprylic/capric triglyceride;

(iii) about 4%, by weight, of steareth-20;

(iv) about 0.8%, by weight, of steareth-2;

(v) about 5%, by weight, of cetyl alcohol;

(vi) about 5%, by weight, of stearyl alcohol;

(vii) about 72%, by weight, of water;

(viii) about 0.3% of xanthan gum;

(ix) about 0.1%, by weight, of propylparaben, about 0.2%, by weight, of methylparaben, and about 1%, by weight, of benzyl alcohol;

(x) about 0.1%, by weight, of butylated hydroxytoluene; and (xi) about 0.05%, by weight, of edetate disodium.

18. A method of claim 15, wherein said method comprises a method of mitigating fine wrinkles in a human.

19. A method of claim 16, wherein said method comprises a method of mitigating fine wrinkles in a human.

20. A method of claim 17, wherein said method comprises a method of mitigating fine wrinkles in a human.

21. A method of claim 18, wherein said emulsion comprises about 0.02%, by weight, of tretinoin.

22. A method of claim 19, wherein said emulsion consists of about 0.02%, by weight, of tretinoin.

23. A method of claim 20, wherein said emulsion consists of about 0.02%, by weight, of tretinoin.

24. A method of claim 18, wherein said emulsion consists of about 0.05%, by weight, of tretinoin.

25. A method of claim 19, wherein said emulsion consists of about 0.05%, by weight, of tretinoin.

26. A method of claim 20, wherein said emulsion consists of about 0.05%, by weight, of tretinoin.

* * * * *